United States Patent [19]

Edwards

[11] Patent Number: 4,699,895
[45] Date of Patent: * Oct. 13, 1987

[54] PROCESS FOR THE MANUFACTURE OF CATALYSTS FOR THE PRODUCTION OF MALEIC ANHYDRIDE

[75] Inventor: Robert C. Edwards, Naperville, Ill.

[73] Assignee: Standard Oil Company (Indiana), Chicago, Ill.

[ * ] Notice: The portion of the term of this patent subsequent to May 7, 2002 has been disclaimed.

[21] Appl. No.: 729,470

[22] Filed: May 1, 1985

Related U.S. Application Data

[63] Continuation-in-part of Ser. No. 537,983, Sep. 30, 1983, Pat. No. 4,515,904.

[51] Int. Cl.[4] .................... B01J 27/198; B01J 31/00; B01J 27/188; B01J 27/19
[52] U.S. Cl. .................................... 502/209; 502/162; 502/172; 502/210; 502/211; 502/212; 502/213; 423/305; 423/306; 549/259; 549/260
[58] Field of Search ............... 502/162, 209, 210, 211, 502/212, 213, 172; 423/305, 306

[56] References Cited

U.S. PATENT DOCUMENTS

| | | | |
|---|---|---|---|
| 3,293,268 | 12/1966 | Bergman et al. | 549/259 |
| 3,296,282 | 1/1967 | Ken | 549/259 |
| 3,832,359 | 8/1974 | Freerke et al. | 502/209 |
| 3,862,146 | 1/1975 | Boghosian | 549/259 |
| 3,867,411 | 2/1975 | Roffelson et al. | 502/209 X |
| 3,888,886 | 6/1975 | Young et al. | 502/209 X |
| 3,907,833 | 9/1975 | Slinkaid et al. | 549/260 X |
| 3,972,832 | 8/1976 | Butler et al. | 502/77 |
| 3,985,775 | 10/1976 | Harrison | 502/209 X |
| 4,092,269 | 5/1978 | Mount et al. | 502/209 |
| 4,132,670 | 1/1979 | Katsumoto et al. | 423/305 X |
| 4,147,661 | 4/1979 | Higgins et al. | 502/209 |
| 4,149,992 | 4/1979 | Mount et al. | 502/209 |
| 4,151,116 | 4/1979 | McDermott | 502/204 |
| 4,154,703 | 5/1979 | Umemura et al. | 502/209 |
| 4,222,945 | 9/1980 | Higgins et al. | 502/209 X |
| 4,276,222 | 6/1981 | Mount et al. | 502/209 X |
| 4,283,288 | 8/1981 | Udovich et al. | 502/209 |
| 4,293,498 | 10/1981 | Lemonski et al. | 549/259 |
| 4,317,778 | 3/1982 | Blum et al. | 549/259 |
| 4,328,126 | 5/1982 | Udovich et al. | 502/209 |
| 4,337,174 | 6/1982 | Mount et al. | 502/209 |
| 4,351,773 | 9/1982 | Milberger et al. | 502/209 X |
| 4,361,501 | 11/1982 | Blum et al. | 502/209 |
| 4,371,457 | 2/1983 | Chu | 502/209 X |
| 4,392,986 | 7/1983 | Yang et al. | 502/209 |
| 4,416,803 | 11/1983 | Udovich et al. | 549/259 X |
| 4,435,521 | 3/1984 | Yang et al. | 502/209 |
| 4,515,899 | 5/1985 | Click et al. | 502/209 |

FOREIGN PATENT DOCUMENTS 1071647  2/1980  Canada .................... 549/259

Primary Examiner—Andrew H. Metz
Assistant Examiner—William G. Wright
Attorney, Agent, or Firm—Matthew R. Hooper; William C. Magidson; Ralph C. Medhurst

[57] ABSTRACT

A process for the manufacture of a phosphorus-vanadium and phosphorus-vanadium co-metal catalysts suitable for use in the manufacture of maleic anhydride from benzene, butane, and other $C_4$ hydrocarbons which process comprises reacting at a temperature of about 0° C. to about 200° C. a vanadium compound in an organic ether solvent having about 2 to about 10 carbon atoms with a phosphoryl halide in the presence of water or an aliphatic alcohol having from about 1 to about 8 carbon atoms, eliminating the solvent and activating the catalyst by the addition of the hydrocarbon feedstock and water and a phosphorus compound at a temperature of about 300° C. to about 500° C. wherein the amount of water added is about 1000 parts per million to about 40,000 parts per million by weight of the reactor feed gas stream is disclosed. The catalysts are useful for the manufacture of maleic anhydride from butane, benzene, and other $C_4$ hydrocarbon feedstocks.

36 Claims, No Drawings

PROCESS FOR THE MANUFACTURE OF CATALYSTS FOR THE PRODUCTION OF MALEIC ANHYDRIDE

BACKGROUND OF THE INVENTION

This is a continuation-in-part application of Ser. No. 537,983 filed on Sept. 30, 1983 U.S. Pat. No. 4,515,904.

FIELD OF THE INVENTION

The field of this invention relates to novel catalysts and to processes for the manufacture of phosphorus-vanadium, and phosphorus-vanadium co-metal catalysts suitable for the oxidation of benzene, butane, butene and butadiene to maleic anhydride.

BACKGROUND

Maleic anhydride is of significant commercial interest throughout the world and is extensively used in the manufacture of alkyd resins. It is also a versatile intermediate for chemical synthesis. Consequently, large quantities of maleic anhydride are produced each year to satisfy these needs.

In general, catalysts proposed for the oxidation of butane to maleic anhydride have been based upon vanadium and phosphorus. In U.S. Pat. No. 3,293,268, it is disclosed that the oxidation of butane to maleic anhydride can be performed in the presence of a phosphorus-vanadium-oxygen-containing complex catalyst. Though this catalyst is capable of oxidizing butane, it does not give sufficiently high yields. Yields of maleic anhydride of only 30 to 50 weight percent are reported. Various activators, stabilizers and promoters have been disclosed in the prior art to improve the yields of maleic anhydride. References include U.S. Pat. Nos. 3,867,411; 3,832,359; 3,888,886; 4,002,650; 4,147,661; 4,149,992; 4,151,116; 4,152,338; 4,152,339; 4,403,943; 4,154,703; and British Application No. 2,019,839A. While the aforementioned prior art tends to bring about some improvement in the performance of the phosphorus-vanadium catalyst, there remains much room for improvement, particularly from the standpoint of high conversion, yield, and catalyst life. Other references of interest include U.S. Pat. Nos. 4,020,174; 4,094,816; 4,089,807; 3,296,282; 3,474,041 and British patent No. 1,464,198. All these references relate to catalyst regeneration and not to new catalyst preparation.

The object of the present invention is to provide a process for the manufacture of phosphorus-vanadium, and phosphorus-vanadium co-metal oxide catalysts by carrying out the reaction in an organic solvent using phosphoryl halides as a source of phosphorus and activating the catalysts with alkyl esters of phosphoric acid or other phosphorus-containing moieties and water. A further object is to provide a process for the manufacture of maleic anhydride in the presence of the catalyst manufactured by the novel process.

Our catalyst is suitably prepared in organic solvents by slurrying vanadium compounds and metals or metal oxides such as molybdenum oxide, zinc oxide, uranium oxide, tungsten oxide, tin oxide, bismuth oxide, titanium oxide, niobium oxide, antimony oxide and cobalt oxide in organic solvents, preferably organic ether solvents.

A small amount of water or a hydrogen donor compound, such as a lower alcohol, is also present in the ether. Suitable alcohols are ethanol and methanol and suitable ethers are tetrahydrofuran (THF), tetrahydropyran, 1,2-dimethoxyethane, bis(2-methoxyethyl)ether, 1,4-dioxane, ethylether, propylether, butylether, and pentylether. Phosphoryl halide is slowly added to the slurry. The water or hydrogen donor reacts with the phosphoryl halide to generate anhydrous phosphoric acid or phosphate esters and hydrogen halide gas. The hydrogen halide dissolves both the vanadium compound and the co-metal compound and also reduces the vanadium from a valence state of five to a valence state of about four. This reaction takes place at a temperature of about 0° C. to about 200° C.

While the reaction solution is being refluxed, optimally, a modifier or mixture of modifiers such as o-xylene, m-xylene, p-xylene, benzene, toluene, mesitylene, pseudocumene, phthalic anhydride, trimellitic anhydride, benzoic acid, toluic acid, phthalic acid, isophthalic acid, terephthalic acid, trimesic acid, or trimellitic acid, is suitably added to the reaction solvent. After refluxing, the color of the solution is green. The volume of the solution is reduced by distillation or evaporation until it becomes a thick syrup. This syrup is dried at a temperature of about 120° C. to about 150° C. and 0-15 inches of mercury vacuum under an air purge. Once dry, the color of the solid material is brown. The catalyst can be formed into geometric forms, such as cylinders, using graphite, Sterotex, or other lubricants such as stearic acid, zinc stearate or starch and binders such as polyvinyl alcohol. The catalyst in the form of geometric shapes or in powder form is suitably calcined in air or a nitrogen-air combination before loading into a suitable tubular reactor. The catalyst is activated further by the addition of water and phosphorus compounds or mixtures thereof such as alkylphosphates, phosphites, and phosphines. This activation takes place at a temperature of about 300° C. to about 500° C. Representative phosphorus compounds have the following structures:

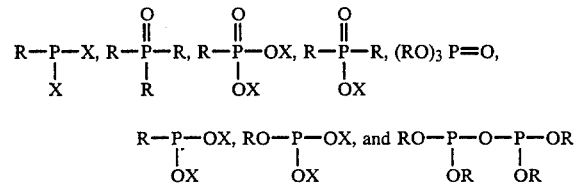

wherein R is phenyl or an alkyl radical of 1 to 6 carbon atoms and X is H or R. Suitable compounds are primary, $RPH_2$, secondary, $R_2PH$, and tertiary, $R_3P$, phosphines, such as ethyl phosphine; the tertiary phosphine oxides, $R_3PO$, such as tripropyl phosphine oxide; the primary, $RP(O)(OX)_2$, and secondary, $R_2P(O)OX$, phosphonic acids, such as benzene phosphonic acid; the esters of the phosphonic acids, such as diethyl methanephosphonate; the phosphonous acids, $RPO_2X_2$, such as benzenephosphonous acid and the esters thereof, such as the monoethyl ester; the phosphinous acids, $R_2POX$, such as diethyl phosphinous acid and the esters thereof, such as the monoethyl ester; the primary, $ROP(OX)_2$, secondary, $(RO)_2POX$, and tertiary, $(RO)_3P$, phosphites, such as diethyl phosphite, trimethyl phosphite, triethyl phosphite, triisopropyl phosphite, tripropyl phosphite and tributyl phosphite, and the pyrophosphites, such as tetraethyl pyrophosphite. The preferred phosphorus compound is an ester of orthophosphoric acid having the formula $(RO)_3P=O$ wherein R is hydrogen or a $C_1$-$C_4$ alkyl, at least one R being a $C_1$-$C_4$ alkyl. The preferred phosphorus compounds are triethylphosphate and trimethylphosphate.

Our catalyst has a much higher yield of maleic anhydride from butane feedstock than catalysts of the prior art, such as those disclosed in U.S. Pat. Nos. 3,862,146 and 4,328,126. Among the many advantages of our novel process for the manufacture of the catalyst can be cited the quantitative use of the expensive vanadium, the use of phosphoryl halides as a source of phosphorus, and inexpensive solvents such as organic ethers in combination with small amounts of water, methanol or ethanol.

The novel catalyst comprises a phosphorus-vanadium mixed oxide or a phosphorus-vanadium mixed oxide promoted by metals. The atomic ratio of the vanadium to phosphorus can suitably be in the range of 0.5:1 to 1.25:1.0. The total atomic ratio of vanadium to phosphorus advantageously is in the range of 0.75:1 to 1:1. It is preferred that the total atomic ratio of molybdenum, zinc, tungsten, uranium, tin, bismuth, titanium, niobium or cobalt to vanadium should be in the range of 0.001:1 to 0.2:1. The atomic ratio of phosphorus to vanadium is suitably in the range of 0.8:1 to 2:1, preferably 1:1 to 1.3:1.

The co-metal, such as molybdenum, zinc, tungsten, uranium, bismuth, titanium, antimony, niobium, cobalt or tin, may be added as a compound together with vanadium, or separately introduced into the solution. Suitable co-metal compounds comprise their oxides and soluble salts. Suitable molybdenum compounds comprise molybdenum oxide and most soluble molybdenum salts. If it is desired to improve physical properties of the catalysts, they may be treated with the suspension of an inert support, for example, alumina, titania, silicon carbide, kieselguhr, pumice, or silica. The catalyst may be reinforced with such materials at any stage in its preparation.

According to our process, the average valence of vanadium is in the range of about 3.8 to 4.2. In our catalyst preparation various phosphoryl halides may be used, but $POCl_3$ is preferred. The catalyst can be activated with water and:

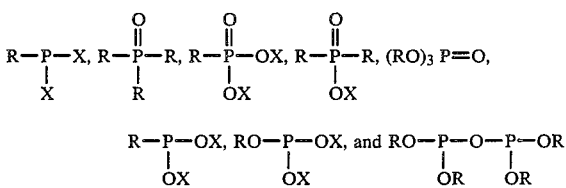

wherein R is phenyl or an alkyl radical of 1 to 6 carbon atoms and X is H or R. Suitable compounds are the primary, $RPH_2$, secondary, $R_2PH$, and tertiary, $R_3P$, phosphines, such as ethyl phosphine; the tertiary phosphine oxides, $R_3PO$, such as tripropyl phosphine oxide; the primary, $RP(O)(OX)_2$, and secondary, $R_2P(O)OX$, phosphonic acids, such as benzene phosphonic acid; the esters of the phosphonic acids, such as diethyl methanephosphonate; the phosphonous acids, $RPO_2X_2$, such as benzenephosphonous acid and the esters thereof such as the monoethyl ester; the phosphinous acids, $R_2POX$, such as diethyl phosphinous acid and the esters thereof, such as the monoethyl ester; the primary, $ROP(OX)_2$, secondary, $(RO)_2POX$, and tertiary, $(RO)_3P$, phosphites, such as diethyl phosphite, trimethyl phosphite, triethyl phosphite, triisopropyl phosphite, tripropyl phosphite and tributyl phosphite, and the pyrophosphites, such as tetraethyl pyrophosphite. The preferred phosphorus compound is an ester of orthophosphoric acid having the formula $(RO)_3P=O$ wherein R is hydrogen or a $C_1-C_4$ alkyl, at least one R being a $C_1-C_4$ alkyl. The preferred phosphate compounds are triethylphosphate and trimethylphosphate.

The amount of water added is about 1000 to about 40,000 parts per million by weight of the reactor feed gas stream. The reactor feed gas stream comprises hydrocarbon and air.

Suitable vanadium compounds include: vanadium oxides, such as vanadium pentoxide, vanadium trioxide and the like; vanadium oxyhalides, such as vanadyl chloride, vanadyl dichloride, vanadyl trichloride, vanadyl bromide, vanadyl dibromide, vanadyl tribromide and the like; vanadium-containing acids, such as metavanadic acid, pyrovanadic acid and the like; vanadium salts, such as ammonium meta-vanadate, vanadium sulfate, vanadium phosphate, vanadyl formate, vanadyl oxalate and the like; however, vanadium pentoxide is preferred.

This invention also comprises a process for oxidizing butane to maleic anhydride by contacting it in the presence of oxygen with the novel catalyst. The oxidation of butane to maleic anhydride may be accomplished by contacting n-butane in low concentration in oxygen with the described catalyst. Air is entirely satisfactory as a source of oxygen, but synthetic manufactures of oxygen and diluent gases, such as nitrogen, also may be employed. Air enriched with oxygen may be used.

The gaseous feed stream to the oxidation reactors will normally contain air and about 0.2 to about 1.7 mole percent of n-butane. About 0.8 to 1.5 mole percent of n-butane is satisfactory for optimum yield of maleic anhydride for the process of this invention. Although higher concentrations may be employed, explosive hazards may be encountered. Lower concentrations of butane, less than about one percent, of course, will reduce the total yield obtained at equivalent flow rates and, thus, are not normally economically employed. The flow rate of the gaseous stream through the reactor may be varied within rather wide limits, but the preferred range of operations is at the rate of about 100 to 4000 cc of feed per cc of catalyst per hour, and more preferably about 1000 to 2400 cc of feed per cc of catalyst per hour. Residence times of the gas stream will normally be less than about four seconds, more preferably less than about one second, and down to a rate where less efficient operations are obtained. The flow rates and residence times are calculated at standard conditions of 760 mm of mercury at 0° C. A variety of reactors will be found to be useful, and multiple tube heat exchanger-type reactors are quite satisfactory. The tops of such reactors may vary in diameter from about one-quarter inch to about three inches, and the length may be varied from about three to about ten or more feet. The oxidation reaction is an exothermic reaction and, therefore, relatively close control of the reaction temperatures should be maintained. It is desirable to have the surface of the reactors at relatively constant temperatures, and some medium to conduct heat from the reactors is necessary to aid temperature control. Such media may be Woods metal, molten sulfur, mercury, molten lead and the like, but it has been found that eutectic salt baths are completely satisfactory. One such salt bath is a sodium nitrate-sodium nitrite-potassium nitrate eutectic constant temperature mixture. An additional method of temperature control is to use a metal block reactor whereby the metal surrounding the tube acts as a temperature-regulating body. As will be recognized by one skilled in the art, the heat-exchanger medium may be kept at the proper temperature by heat exchangers and the like. The reactor or reaction tubes may be iron, stainless steel, carbon steel, nickel, glass tubes such as vycor and the like. Both carbon steel and nickel tubes have excellent long life under the conditions of the reaction described herein. Normally, the reactors contain a preheat zone under an inert material such as one-quarter-inch alundum pellets, inert ceramic balls, nickel balls, or chips and the like present at about one-half to one-tenth the volume of the active catalyst present.

The temperature of reaction may be varied within some limits, but normally the reaction should be conducted at a temperature within a rather critical range. The oxidation reaction is exothermic and once reaction is underway, the main purpose of the salt bath or other media is to conduct heat away from the walls of the reactor and control the reaction. Better operations are normally obtained when the reaction temperature employed is no greater than 20°–50° F. above the salt bath temperature. The temperature of the reactor, of course, will also depend to some extent upon the size of the reactor and the benzene, butane, butene or butadiene concentration.

The reaction may be conducted at atmospheric, superatmospheric, or subatmospheric pressure. The exit pressure will be at least slightly higher than the ambient pressure to ensure a positive flow from the reactor. The pressure of the inert gases must be sufficiently high to overcome the pressure drop through the reactor.

Maleic anhydride may be recovered by a number of ways well-known to those skilled in the art. For example, the recovery may be by direct condensation or by absorption in suitable media, with specific operations and purification of the maleic anhydride. The following examples will serve to provide full understanding of the invention, but it is to be understood that these examples are given for illustrative purposes only and will not be interpreted as limiting the invention in any way. In the Examples, the terms "conversion", "selectivity" and "yield" are defined as follows:

$$\text{Conversion \%} = \frac{\text{Moles n-butane reacted}}{\text{Moles n-butane in feed}} \times 100$$

$$\text{Selectivity \%} = \frac{\text{Moles maleic anhydride produced}}{\text{Moles n-butane feed consumed}} \times 100$$

$$\text{Yield Wt. \%} = (\text{Conversion}) \times (\text{Selectivity}) \times 169$$

EXAMPLE 1

To a 3-liter, 3-neck, round-bottom flask equipped with a thermowell, electrical mantle, mechanical stirrer, and reflux condenser, were added 91 g of $V_2O_5$, 4.4 g of $MoO_3$, 196.3 g of $POCl_3$, and 500 ml of tetrahydrofuran (THF). Water, 69 g, was slowly added from a dropping funnel to the slurry causing the $V_2O_5$ to dissolve and the solvent to reflux. The red-brown solution was refluxed at 103° C. for 13.5 hours reducing the vanadium (V) to vanadium (IV) and turning the color green.

The solvent was distilled from the green solution until a thick syrup remained. The syrup was put in a vacuum oven overnight at 10 in. of Hg vacuum and 130° C. with a slight air purge passing through the oven. The dry catalyst precursor which was brown in color was ground and formed into 3/16" cylindrical tablets using 5 wt. % graphite as a lubricant. The side crush strength of the tablets was 6.5–7.5 lbs.

A 6 $cm^3$ charge of the tablets was loaded into a 0.62" diameter minireactor and evaluated with a feed of 1.1% n-butane in synthetic air at 1200 VHSV. About 10,000 ppm of water were continually added to the reactor feed stream by passing it through a water saturator. This catalyst gave a maximum maleic anhydride yield of 103 wt. % at a temperature of 741° F. after 53 days on stream. The conversion was 89 mole % and the selectivity 69 mole %. The surface area of this catalyst was 40 $m^2/g$ and the pore volume by adsorption was 0.215 cc/g.

EXAMPLE 2

A catalyst precursor was prepared in a similar manner as described in Example 1 except that the solution was refluxed for 11.5 hours. The dried powder was ground, mixed with 5 wt. % graphite, and formed into 3/16" cylinders having a 6.5–8.0 lb. side crush strength. These tablets were calcined to 700° F. in air before being charged into a minireactor and evaluated as reported in Example 1. This catalyst gave a maximum maleic anhydride yield of 102 wt. % at 745° F. The conversion was 90 mole % and the selectivity 67 mole %.

EXAMPLE 3

A catalyst precursor was prepared as reported in Example 1 except that the solution was refluxed for only 5 hours and 184 g of $POCl_3$ were used giving a 1.2/1 P/V ratio instead of 1.28/1 as used in Examples 1 and 2. The powder was mixed with 5 wt. % graphite and formed into 3/16" cylinders having a 6–7 lb. side crush strength.

The catalyst was evaluated in a minireactor as described in Example 1. The catalyst gave a maximum maleic anhydride yield of 100 wt. % at 753° F. with an 89 mole % conversion and a 66 mole % selectivity.

EXAMPLE 4

A catalyst precursor was prepared in a similar manner as in Example 1. Phthalic anhydride, 22 g, was added to the solution which was refluxed for 12.5 hours. The powder was mixed with 5 wt. % graphite and formed into 3/16" cylindrical tablets having a 6–7.5 lb. side crush strength.

The catalyst was evaluated in a minireactor as described in Example 1. A maximum maleic anhydride yield of 100 wt. % was obtained at 741° F. The conversion was 85 mole % and the selectivity 70 mole %. The catalyst surface area was 42 $m^2/g$ and the pore volume by adsorption was 0.2787 cc/g.

EXAMPLE 5

A 12-liter, 3-neck, round-bottom flask equipped with an electrical mantle, mechanical stirrer, thermowell, and reflux condenser was charged with 2 liters of THF, 364 g of $V_2O_5$, 17.6 g of $MoO_3$, and 767 g of $POCl_3$. Water, 270 g, was added slowly causing the $V_2O_5$ to dissolve and turning the solution red-brown. The solution was refluxed for 14.5 hours with the color changing from red-brown to green. Solvent was removed by distillation until the temperature reached 129° C. The thick syrup was put into a vacuum oven at 3–5 in. Hg vacuum and 130° C. with a slight air purge passing through the oven. The dry material was ground, mixed with 5 wt. % graphite, and formed into 3/16" cylindrical tablets having a 5-15 lb. side crush strength. The tablets were calcined in air to 371° C.

This catalyst, 120 g, was loaded into a pilot plant having a 0.62" diameter reactor. After 1219 hours on stream, the catalyst gave a maximum maleic anhydride yield of 77 wt. % at 1.5% n-butane in air feed, 2000 VHSV, and 707° F. salt bath temperature. The feed stream was then passed through a saturator containing a solution of 0.4 g triethylphosphate per liter of water. In this manner, about 10,000 ppm of water were added to the feed stream. The catalyst gave a maximum maleic anhydride yield of 87 wt. % at the same conditions and a salt bath temperature of 725° F. after 1723 hours on stream. Thus, the addition of water and triethylphosphate in small quantities to the feed stream resulted in improving the catalyst yield by 10 wt. %. The concentration of the saturator solution was increased to 0.7 g triethylphosphate per liter of water. After 2395 hours on stream, the yield of maleic anhydride was 89 wt. % at the same conditions and a salt bath temperature of 722° F.

EXAMPLE 6

Using the same experimental setup as described in Example 5, 2 liters of THF, 364 g of $V_2O_5$, 17.3 g of $MoO_3$, and 270 g of water were charged to the large flask. $POCl_3$, 767 g, was added slowly to the mixture causing the $V_2O_5$ to dissolve and turning the color of the solution red-brown. At this time 500 ml of o-xylene were added to the solution and it was refluxed for 16.5 hours causing the solution color to change to green. The solvent was then removed by distillation until the temperature of the catalyst syrup reached 139° C. The syrup was placed into a vacuum oven overnight at 150° C. and 5 in. of Hg vacuum with a slight air purge passing through the oven. The dry brown material was ground, mixed with 5 wt. % graphite, and formed into 3/16" cylindrical tablets having a 3 lb. side crush strength.

A 6 $cm^3$ charge of the tablets was evaluated in a minireactor as described in Example 1. This catalyst gave a maximum maleic anhydride yield of 101 wt. % at 778° F. after 22 days on stream. The conversion was 90 mole % and the selectivity was 66.5 mole %.

This example illustrates that an excellent catalyst can be prepared by adding $POCl_3$ to the reaction mixture which contains a hydrogen donor compound. This method of addition gives better temperature control of the exothermic reaction. Also, the use of the modifier o-xylene, a higher distillation temperature, and a longer reflux time are demonstrated in this Example.

EXAMPLE 7

Using the experimental setup described in Example 1, 91 g of $V_2O_5$, 4.3 g of $MoO_3$, 184 g of $POCl_3$, and 500 ml of THF were charged to the reaction flask. Water, 65 g, was slowly added over 1 hour to the flask causing the vanadium to dissolve and form a red-brown solution. O-xylene, 150 ml, was added to the reaction solution and it was refluxed for 20.5 hours. Solvent was removed by distillation until the temperature of the catalyst syrup reached 151° C. The syrup was dried overnight in a vacuum oven at 140° C. at 0 in. of Hg vacuum with an air purge passing through the oven.

The dried material was ground, mixed with 5 wt. % graphite, and formed into 3/16" cylinders having a 3 lb. side crush strength. The catalyst was evaluated as described in Example 1. The catalyst having a P/V ratio of 1.2/1 gave a maximum maleic anhydride yield of 100 wt. % at 727° F. after 42 days on stream.

EXAMPLE 8

A catalyst was prepared and evaluated as reported in Example 7 except that 11.8 g of zinc metal was used in the catalyst preparation instead of $MoO_3$. This catalyst gave a maximum maleic anhydride yield of 86 wt. % at 822° F. after 50 days on stream.

EXAMPLE 9

A catalyst was prepared and evaluated as described in Example 7 except that 6.96 g of $WO_3$ instead of $MoO_3$ were used in the preparation and the $POCl_3$ was added to the reaction mixture containing the water. This catalyst gave a maximum maleic anhydride yield of 88 wt. % at 736° F. after 49 days on stream.

EXAMPLE 10

A catalyst was prepared and evaluated as described in Example 9 except that 23.19 g of $WO_3$ was used in the preparation. The catalyst gave a maximum maleic anhydride yield of 83 wt. % at 763° F. after 21 days on stream.

EXAMPLE 11

A catalyst was prepared and evaluated as reported in Example 9 except that Sn metal, 3.56 g, was used in place of $WO_3$. The catalyst gave a maximum maleic anhydride yield of 81 wt. % at 761° F. after 29 days on stream.

EXAMPLE 12

A catalyst was prepared and evaluated as described in Example 9 except that $Co_2O_3$, 2.49 g, was used in place of $WO_3$. The catalyst gave a maximum maleic anhydride yield of 87 wt. % at 759° F. after 30 days on stream.

Examples 9-12 show that phosphorus-vanadium catalysts prepared with co-metals other than molybdenum will give excellent yields of maleic anhydride.

EXAMPLE 13

After the catalyst in Example 9 was on stream for 55 days, the feed gas was passed through a saturator containing a 20 wt. % aqueous solution of triethylphosphate. The yield from this catalyst increased to 92 wt. % at 737° F. 10 days later. This treatment improved the yield of this catalyst by 4 wt. %.

EXAMPLE 14

After 27 days on stream, the feed gas to the catalyst in Example 10 was passed through a saturator containing a 1-5 wt. % aqueous solution of triethylphosphate. The yield increased to 97 wt. % at 752° F. 18 days later which is a 14 wt. % improvement in the yield of this catalyst.

EXAMPLE 15

The feed gas to the catalyst in Example 12 was passed through a saturator containing a 1-5 wt. % aqueous solution of triethylphosphate after 31 days on stream. The yield increased to 90 wt. % at 759° F. 7 days later for an improvement in yield of 3 wt. %.

Examples 13-15 illustrate that phosphorus-vanadium catalysts having co-metals other than molybdenum, and prepared according this invention, will give improved yields when treated in situ with phosphorus compounds and water.

EXAMPLE 16

A catalyst was prepared as described in Example 6. The dried catalyst was crushed and calcined in air to 371° C. The calcined powder was mixed with 5 wt. % graphite and formed into 3/16" by 3/16" cylindrical tablets having a 5-6 lb. side crush strength. This catalyst, 136 g, was charged to a pilot plant having a 0.62" internal diameter reactor. The performance of this catalyst at 1.5% n-butane in air feed and 2000 VHSV is summarized in Table I.

TABLE I

| | Performance of Catalyst from Example 16 | | | | |
|---|---|---|---|---|---|
| Hours on Stream | Salt Bath Temp., °F. | Triethylphosphate in the feed, ppm | Water in the feed, ppm | Conv., % | Yield Wt. % |
| 450 | 777 | 0 | 0 | 81 | 78 |
| 642 | — | 5 | 10,000 | — | — |
| 786 | — | 10 | 10,000 | — | — |
| 858 | 742 | 10 | 10,000 | 80 | 80 |
| 1050 | 746 | 10 | 10,000 | 76 | 84 |
| 1146 | 750 | 10 | 10,000 | 82 | 86 |
| 1170 | — | 15 | 10,000 | — | — |
| 1386 | — | 17.5 | 10,000 | — | — |
| 1674 | 777 | 17.5 | 10,000 | 83 | 88 |

After 450 hours on stream, the catalyst gave a maximum maleic anhydride yield of 78 wt. % (81% conversion) at 777° F., 2000 VHSV, and 1.5 mole % n-butane in air feed. Using an Isco metering pump, 10,000 ppm of water and 5 ppm of triethylphosphate were added to the reactor feed at 642 hours. The triethylphosphate concentration was increased to 10 ppm at 786 hours. At 858 hours, the yield improved to 80 wt. % and to 86 wt. % after 1146 hours. A further increase in triethylphosphate to 17.5 ppm at 1386 hours produced an 88 wt. % yield at 1674 hours on stream with 83% conversion, 2000 VHSV, 1.5 mole % n-butane in air feed, and 777° F. salt bath temperature.

This Example illustrates that activation of this catalyst with triethylphosphate and water added to the n-butane and air feed produces a 10 wt. % improvement in maleic anhydride yield.

EXAMPLE 17

A catalyst precursor was prepared according to the process in Example 6. The dried material was crushed and calcined in air to 371° C. The calcined powder was mixed with 5 wt. % graphite and formed into 3/16" by 3/16" cylindrical tablets having a 4-6 lb. side crush strength. This tableted catalyst, 138 g, was charged to a pilot plant having a 0.62" internal diameter reactor. The performance of this catalyst at 1.5% n-butane in air feed and 2000 VHSV is summarized in Table II.

TABLE II

| | Performance of Catalyst from Example 17 | | | | |
|---|---|---|---|---|---|
| Hours on Stream | Salt Bath Temp., °F. | Triethylphosphate in the feed, ppm | Water in the feed, ppm | Conv., % | Yield, Wt. % |
| 262 | 772 | 0 | 0 | 77 | 77 |
| 740 | — | 10 | 0 | — | — |
| 1004 | 751 | 10 | 0 | 81 | 73 |
| 1028 | — | 10 | 10,000 | — | — |
| 1076 | 762 | 10 | 10,000 | 77 | 83 |
| 1244 | 763 | 10 | 10,000 | 82 | 87 |
| 1412 | — | 7 | 10,000 | — | — |
| 1508 | 754 | 7 | 10,000 | 81 | 88 |
| 1772 | — | 8 | 10,000 | — | — |
| 1844 | 760 | 8 | 10,000 | 83 | 85 |
| 1868 | — | 0 | 10,000 | — | — |
| 2272 | 721 | 0 | 10,000 | 81 | 74 |

The catalyst gave a maximum maleic anhydride yield of 77 wt. % (77% conversion) after 262 hours on stream with no water and triethylphosphate addition to the feed. At 740 hours, 10 ppm of triethylphosphate were added to the feed using an Isco metering pump keeping the VHSV at 2000 and 1.5% n-butane in air feed. In this case, the catalyst yield did not increase as occurred in Example 16 when both triethylphosphate and water were added to the feed during activation. At 1004 hours, the yield was only 73 wt. % despite the addition of 10 ppm of triethylphosphate to the feed for 364 hours. Water, 10,000 ppm, was then introduced into the feed with an Isco metering pump along with 10 ppm of triethylphosphate at 1028 hours. Only 48 hours at these conditions produced an 83 wt. % yield of maleic anhydride. An 88 wt. % yield of maleic anhydride was achieved at 1508 hours with 7 ppm of triethylphosphate and 10,000 ppm of water being added to the feed. The triethylphosphate was removed from the feed at 1868 hours. By 2272 hours, the yield had declined to 74 wt. %.

This Example shows that the addition of both triethylphosphate and water to the feed during catalyst activation is required to significantly improve the catalyst yield. Catalyst activation with n-butane and air feed and either triethylphosphate or water alone does not significantly improve the catalyst yield.

EXAMPLE 18

Using the same experimental setup described in Example 5, 1 liter of THF, 364 g of $V_2O_5$, 17.3 g of $MoO_3$, and 270 g of water were charged to the large flask. $POCl_3$, 767 g, was added dropwise from an addition funnel over a 2.5-hour time period causing the $V_2O_5$ to dissolve and turning the solution red-brown. The contents of the flask were allowed to reflux for 2 hours following the end of the $POCl_3$ addition. The temperature of the flask contents during reflux was 93°–111° C. At this time, about 700 ml of solvent were removed by distillation leaving a dark green syrup. The syrup was dried in an air-ventilated oven at 148° C. and 1-5 in. of Hg vacuum. The dried brown material was crushed and calcined in air to 371° C. The calcined powder was mixed with 5 wt. % graphite and formed into 3/16" by 3/16" cylindrical tablets having a 5 lb. side crush strength. These tablets, 130 g, were charged to a pilot plant having a 0.62" internal diameter reactor. The performance of this catalyst at 1.5% n-butane in air feed and 2000 VHSV is reported in Table III.

TABLE III

| | Performance of Catalyst from Example 18 | | | | |
|---|---|---|---|---|---|
| Hours on Stream | Salt Bath Temp., °F. | Triethylphosphate in the feed, ppm | Water in the feed, ppm | Conv., % | Yield, Wt. % |
| 235 | 768 | 0 | 0 | 81 | 81 |
| 379 | — | 5 | 10,000 | — | — |

TABLE III-continued

Performance of Catalyst from Example 18

| Hours on Stream | Salt Bath Temp., °F. | Triethylphosphate in the feed, ppm | Water in the feed, ppm | Conv., % | Yield, Wt. % |
|---|---|---|---|---|---|
| 591 | 742 | 5 | 10,000 | 80 | 83 |
| 783 | 750 | 5 | 10,000 | 84 | 89 |
| 903 | 754 | 5 | 10,000 | 81 | 89 |

The catalyst gave a maximum yield of 81 wt. % (81% conversion) at 768° F. with no triethylphosphate or water addition to the feed after 235 hours on stream. Using an Isco metering pump, 5 ppm of triethylphosphate and 10,000 ppm of water were added to the feed at 379 hours. At 591 hours, the maleic anhydride yield was 83 wt. % improving to 89 wt. % at 783 hours.

This Example indicates that an excellent catalyst can be prepared with a lower solvent-to-vanadium ratio, no o-xylene, and a 2-hour reflux of the reaction mixture.

We claim:

1. A process for the manufacture of a phosphorus-vanadium oxide catalyst suitable for use in the manufacture of maleic anhydride from butane which process comprises reacting at a temperature of about 0° C. to about 200° C. a vanadium compound in an organic ether solvent having from about 2 to about 10 carbon atoms, with a phosphoryl halide in the presence of water or an aliphatic alcohol having from about 1 to about 8 carbon atoms, eliminating the solvent and activating the catalyst by the addition of butane, benzene or another $C_4$ hydrocarbon feedstock and water and a phosphorus compound at a temperature of about 300° C. to about 500° C. wherein the amount of water added is about 1000 parts per million to about 40,000 parts per million by weight of the reactor feed gas stream.

2. The process of claim 1 wherein the vanadium compound is vanadium pentoxide.

3. A process for the manufacture of a phosphorus-vanadium oxide catalyst suitable for use in the manufacture of maleic anhydride from butane which process comprises reacting at a temperature of about 0° C. to about 200° C. a vanadium compound in an organic ether solvent having from about 2 to about 10 carbon atoms, with a phosphoryl chloride in the presence of water or an aliphatic alcohol having from about 1 to about 8 carbon atoms, wherein the phosphorus-vanadium oxide catalyst is dissolved and the dissolved phosphorus-vanadium oxide catalyst is solidified by evaporation or distillation of the organic solvent and activating the catalyst by the addition of butane, benzene or another $C_4$ hydrocarbon feedstock and water and a phosphorus compound at a temperature of about 300° C. to about 500° C. wherein the amount of water added is about 1000 parts per million to about 40,000 parts per million by weight of the reactor feed gas stream.

4. The process of claim 1 wherein the ether is tetrahydrofuran.

5. A process for the manufacture of a phosphorus-vanadium oxide catalyst suitable for use in the manufacture of maleic anhydride from butane which process comprises reacting at a temperature of about 0° C. to about 200° C. a vanadium compound in an organic ether solvent having from about 2 to about 10 carbon atoms, with a phosphoryl chloride in the presence of water or an aliphatic alcohol having from about 1 to about 8 carbon atoms, eliminating the solvent and activating the catalyst by the addition of butane, benzene or another $C_4$ hydrocarbon feedstock and water and an alkyl ester of orthophosphoric acid at a temperature of about 300° C. to about 500° C. wherein the amount of water added is about 1000 parts per million to about 40,000 parts per million by weight of the reactor feed gas stream.

6. The process of claim 5 wherein the alkyl ester of orthophosphoric acid has the following structure:

$$(RO)_3P=O$$

wherein R is hydrogen or a $C_1$ to $C_4$ alkyl, at least one R being a $C_1$ to $C_4$ alkyl 7. The process of claim 6 wherein the alkyl ester is triethylphosphate.

8. The process of claim 6 wherein the alkyl ester is trimethylphosphate.

9. A process for the manufacture of a phosphorus-vanadium oxide catalyst suitable for use in the manufacture of maleic anhydride from butane which process comprises reacting at a temperature of about 0° C. to about 200° C. a vanadium compound in an organic ether solvent having from about 2 to about 10 carbon atoms, with a phosphoryl chloride in the presence of water or an aliphatic alcohol having from about 1 to about 8 carbon atoms, eliminating the solvent and activating the catalyst at a temperature of about 300° C. to about 500° C. by the addition of butane, benzene or another $C_4$ hydrocarbon feedstock and water wherein the amount of water added is about 1000 parts per million to about 40,000 parts per million by weight of the reactor feed gas stream and a phosphorus compound selected from the group consisting of:

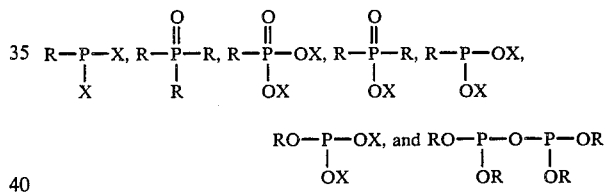

wherein R is phenyl or an alkyl radical of 1 to 6 carbon atoms and X is H or R.

10. A process for the manufacture of a phosphorus-vanadium co-metal oxide catalyst suitable for use in the manufacture of maleic anhydride from butane which process comprises reacting at a temperature of about 0° C. to about 200° C. a vanadium compound in an organic ether solvent having about 2 to about 10 carbon atoms with a phosphoryl halide in the presence of water or an aliphatic alcohol having from about 1 to about 8 carbon atoms, eliminating the solvent and activating the catalyst by the addition of butane, benzene or another $C_4$ hydrocarbon feedstock and water and a phosphorus compound at a temperature of about 300° C. to about 500° C. wherein the amount of water added is about 1000 parts per million to about 40,000 parts per million by weight of the reactor feed gas stream.

11. The process of claim 10 wherein the vanadium compound is vanadium pentoxide.

12. A process for the manufacture of a phosphorus-vanadium co-metal oxide catalyst suitable for use in the manufacture of maleic anhydride from butane, benzene or another $C_4$ hydrocarbon feedstock which process comprises reacting at a temperature of about 0° C. to about 200° C. a vanadium compound in an organic ether solvent having about 2 to about 10 carbon atoms with a phosphoryl chloride in the presence of water or an aliphatic alcohol having from about 1 to about 8 carbon atoms, wherein the phosphorus-vanadium co-metal oxide catalyst is dissolved and the dissolved phosphorus-vanadium co-metal oxide catalyst is solidified by evaporation or distillation of the organic solvent and activating the catalyst by the addition of butane, benzene or another C₄ hydrocarbon feedstock and water and a phosphorus compound at a temperature of about 300° C. to about 500° C. wherein the amount of water added is about 1000 parts per million to about 40,000 parts per million by weight of the reactor feed gas stream.

13. The process of claim 10 wherein the ether is tetrahydrofuran.

14. A process for the manufacture of a phosphorus-vanadium co-metal oxide catalyst wherein the co-metal is selected from the group consisting of zinc, molybdenum, niobium, tungsten, uranium, cobalt and tin suitable for use in the manufacture of maleic anhydride from butane, benzene or another C₄ hydrocarbon feedstock which process comprises reacting at a temperature of about 0° C. to about 200° C. a vanadium compound in an organic ether solvent having about 2 to about 10 carbon atoms with phosphoryl chloride in the presence of water or an aliphatic alcohol having from about 1 to about 8 carbon atoms, eliminating the solvent and activating the catalyst by the addition of butane, benzene or another C₄ hydrocarbon feedstock and water and an alkyl ester of orthophosphoric acid at a temperature of about 300° C. to about 500° C. wherein the amount of water added is about 1000 parts per million to about 40,000 parts per million by weight of the reactor feed gas stream.

15. The process of claim 14 wherein the alkyl ester of orthophosphoric acid has the following structure:

$$(RO)_3P=O$$

wherein R is hydrogen or a C₁ to C₄ alkyl, at least one R being a C₁ to C₄ alkyl.

16. The process of claim 15 wherein the alkyl ester is triethylphosphate.

17. The process of claim 15 wherein the alkyl ester is trimethylphosphate.

18. A process for the manufacture of a phosphorus-vanadium co-metal oxide catalyst suitable for use in the manufacture of maleic anhydride from butane, benzene or another C₄ hydrocarbon which process comprises reacting at a temperature of about 0° C. to about 200° C. a vanadium compound in an organic ether solvent having about 2 to about 10 carbon atoms with a phosphoryl chloride in the presence of water or an aliphatic alcohol having from about 1 to about 8 carbon atoms, eliminating the solvent and activating the catalyst at a temperature of about 300° C. to about 500° C. by the addition of butane, benzene or another C₄ hydrocarbon feedstock and water wherein the amount of water added is about 1000 parts per million to about 40,000 parts per million by weight of the reactor feed gas stream and a phosphorus compound selected from the group consisting of:

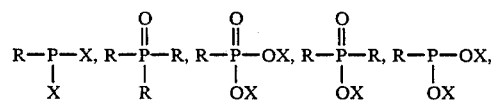

-continued

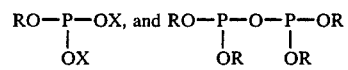

wherein R is phenyl or an alkyl radical of 1 to 6 carbon atoms and X is H or R.

19. A process for the manufacture of a phosphorus-vanadium-molybdenum oxide catalyst suitable for use in the manufacture of maleic anhydride from butane, benzene or another C₄ hydrocarbon feedstock which process comprises reacting at a temperature of about 0° C. to about 200° C. a vanadium compound in an organic ether solvent having about 2 to about 10 carbon atoms with a phosphoryl chloride in the presence of water or an aliphatic alcohol having from about 1 to about 8 carbon atoms, eliminating the solvent and activating the catalyst by the addition of butane, benzene or another C₄ hydrocarbon feedstock and water and a phosphorus compound at a temperature of about 300° C. to about 500° C. wherein the amount of water added is about 1000 parts per million to about 40,000 parts per million by weight of the reactor feed gas stream.

20. The process of claim 19 wherein the vanadium compound is vanadium pentoxide.

21. A process for the manufacture of a phosphorus-vanadium-molybdenum oxide catalyst suitable for use in the manufacture of maleic anhydride from butane, benzene or another C₄ hydrocarbon which process comprises reacting at a temperature of about 0° C. to about 200° C. a vanadium compound in an organic ether solvent having about 2 to about 10 carbon atoms with a phosphoryl chloride in the presence of water or an aliphatic alcohol having from about 1 to about 8 carbon atoms, wherein the phosphorus-vanadium-molybdenum oxide catalyst is dissolved and the dissolved phosphorus-vanadium-molybdenum oxide catalyst is solidified by evaporation or distillation of the organic solvent and activating the catalyst by the addition of butane, benzene or another C₄ hydrocarbon feedstock and water and a phosphorus compound at a temperature of about 300° C. to about 500° C. wherein the amount of water added is about 1000 parts per million to about 40,000 parts per million by weight of the reactor feed gas stream.

22. The process of claim 19 wherein the ether is tetrahydrofuran.

23. A process for the manufacture of a phosphorus-vanadium-molybdenum oxide catalyst suitable for use in the manufacture of maleic anhydride from butane, benzene or another C₄ hydrocarbon feedstock which process comprises reacting at a temperature of about 0° C. to about 200° C. a vanadium compound in an organic ether solvent having about 2 to about 10 carbon atoms with an alkyl ester of orthophosphoric acid in the presence of water or an aliphatic alcohol having from about 1 to about 8 carbon atoms, eliminating the solvent and activating the catalyst by the addition of butane, benzene or another C₄ hydrocarbon feedstock and water and an alkyl ester of orthophosphoric acid at a temperature of about 300° C. to about 500° C. wherein the amount of water added is about 1000 parts per million to about 40,000 parts per million by weight of the reactor feed gas stream.

24. The process of claim 23 wherein the alkyl ester of orthophosphoric acid has the following structure:

$$(RO)_3P=O$$

wherein R is hydrogen or a $C_1$ to $C_4$ alkyl, at least one R being a $C_1$ to $C_4$ alkyl.

25. The process of claim 24 wherein the alkyl ester is triethylphosphate.

26. The process of claim 24 wherein the alkyl ester is trimethylphosphate.

27. A process for the manufacture of a phosphorus-vanadium-molybdenum oxide catalyst suitable for use in the manufacture of maleic anhydride from butane, benzene or another $C_4$ hydrocarbon which process comprises reacting at a temperature of about 0° C. to about 200° C. a vanadium compound in an organic ether solvent having about 2 to about 10 carbon atoms with phosphoryl chloride in the presence of water or an aliphatic alcohol having from about 1 to about 8 carbon atoms, eliminating the solvent and activating the catalyst at a temperature of about 300° C. to about 500° C. by the addition of butane, benzene or another $C_4$ hydrocarbon feedstock and water wherein the amount of water added is about 1000 parts per million to about 40,000 parts per million by weight of the reactor feed gas stream and a phosphorus compound selected from the group consisting of:

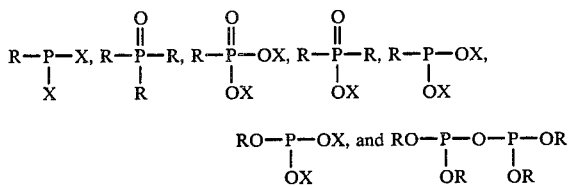

wherein R is phenyl or an alkyl radical of 1 to 6 carbon atoms and X is H or R.

28. A process for the manufacture of a phosphorus-vanadium-zinc oxide catalyst suitable for use in the manufacture of maleic anhydride from butane, benzene or another $C_4$ hydrocarbon feedstock which process comprises reacting at a temperature of about 0° C. to about 200° C. a vanadium compound in an organic ether solvent having about 2 to about 10 carbon atoms with a phosphoryl chloride in the presence of water or an aliphatic alcohol having from about 1 to about 8 carbon atoms, eliminating the solvent and activating the catalyst by the addition of butane, benzene or another $C_4$ hydrocarbon feedstock and water and a phosphorus compound at a temperature of about 300° C. to about 500° C. wherein the amount of water added is about 1000 parts per million to about 40,000 parts per million by weight of the reactor feed gas stream.

29. The process of claim 28 wherein the vanadium compound is vanadium pentoxide.

30. The process of claim 28 wherein the ether is tetrahydrofuran.

31. The process of claim 30 wherein the alkyl ester of orthophosphoric acid has the following structure:

wherein R is hydrogen or a $C_1$ to $C_4$ alkyl, at least one R being a $C_1$ to $C_4$ alkyl.

32. A process for the manufacture of a phosphorus-vanadium-zinc oxide catalyst suitable for use in the manufacture of maleic anhydride from butane, benzene or another $C_4$ hydrocarbon feedstock which process comprises reacting at a temperature of about 0° C. to about 200° C. a vanadium compound in an organic ether solvent having about 2 to about 10 carbon atoms with a phosphoryl chloride in the presence of water or an aliphatic alcohol having from about 1 to about 8 carbon atoms, wherein the phosphorus-vanadium-zinc oxide catalyst is dissolved and the dissolved phosphorus-vanadium-zinc oxide catalyst is solidified by evaporation or distillation of the organic solvent and activating the catalyst by the addition of butane, benzene or another $C_4$ hydrocarbon feedstock and water and a phosphorus compound at a temperature of about 300° C. to about 500° C. wherein the amount of water added is about 1000 parts per million to about 40,000 parts per million,by weight of the reactor feed gas stream.

33. A process for the manufacture of a phosphorus-vanadium-zinc oxide catalyst suitable for use in the manufacture of maleic anhydride from butane which process comprises reacting at a temperature of about 0° C. to about 200° C. a vanadium compound in an organic ether solvent having about 2 to about 10 carbon atoms with phosphoryl chloride in the presence of water or an aliphatic alcohol having from about 1 to about 8 carbon atoms, eliminating the solvent and activating the catalyst by the addition of butane or another hydrocarbon feedstock and an alkyl ester of orthophosphoric acid at a temperature of about 300° C. to about 500° C. wherein the amount of water added is about 1000 parts per million to about 40,000 parts per million by weight of the reactor feed gas stream.

34. The process of claim 32 wherein the alkyl ester is triethylphosphate.

35. The process of claim 32 wherein the alkyl ester is trimethylphosphate.

36. A process for the manufacture of a phosphorus-vanadium-zinc oxide catalyst suitable for use in the manufacture of maleic anhydride from butane which process comprises reacting at a temperature of about 0° C. to about 200° C. a vanadium compound in an organic ether solvent having about 2 to about 10 carbon atoms with a phosphoryl chloride in the presence of water or an aliphatic alcohol having from about 1 to about 8 carbon atoms, eliminating the solvent and activating the catalyst at a temperature of about 300° C. to about 500° C. by the addition of butane, benzene, butadiene or butene or another hydrocarbon feedstock and water wherein the amount of water added is about 1000 parts per million to about 40,000 parts per million by weight of the reactor feed gas stream and a phosphorus compound selected from the group consisting of:

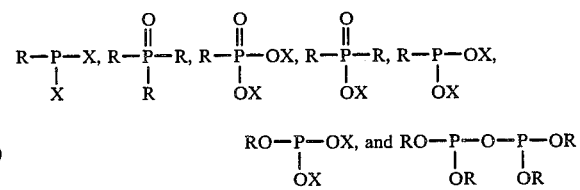

wherein R is phenyl or an alkyl radical of 1 to 6 carbon atoms and X is H or R.

* * * * *